United States Patent [19]
Wehrli et al.

[11] 3,962,217
[45] June 8, 1976

[54] PROCESS FOR THE MANUFACTURE OF $\Delta^{16}$-STEROID-14β,18,20-TRIOLS AND -14β,20-DIOL-18-OLS OF THE PREGNANE SERIES

[75] Inventors: Hansuli Wehrli, Reinach; Oskar Jeger, Zollikerberg, both of Switzerland

[73] Assignee: Ciba-Geigy Corporation, Ardsley, N.Y.

[22] Filed: Nov. 26, 1974

[21] Appl. No.: 527,334

Related U.S. Application Data

[63] Continuation-in-part of Ser. No. 364,466, May 29, 1973, abandoned, which is a continuation-in-part of Ser. No. 82,183, Oct. 19, 1970.

[30] Foreign Application Priority Data

| | | |
|---|---|---|
| Oct. 24, 1969 | Switzerland | 15902/69 |
| July 24, 1970 | Switzerland | 11242/70 |
| May 30, 1972 | Switzerland | 7966/72 |

[52] U.S. Cl. .................. 260/239.55 R; 260/239.57; 260/239.5; 260/397.5
[51] Int. Cl.$^2$ .................. C07J 41/00
[58] Field of Search .................. 260/239.55 R

[56] References Cited

UNITED STATES PATENTS 3,781,271 12/1973 Wehrli et al. .............. 260/239.55 R

FOREIGN PATENTS OR APPLICATIONS 1,212,966 11/1970 United Kingdom .............. 260/397.4

OTHER PUBLICATIONS

Graf et al., "Helv. Chim. Acta," vol. 54 (1971) pp. 2789–2792.
"Steroid Reactions" by Djerassi et al., p. 141, relied on.

*Primary Examiner*—Elbert L. Roberts
*Attorney, Agent, or Firm*—Joseph G. Kolodny; John J. Maitner; Theodore O. Groeger

[57] ABSTRACT

The invention is for a selective reduction of the 20-oxo group in $\Delta^{16}$-steroid-14β,18-diol-20-ones of the pregnane series to form the two epimeric 20-alcohols having the 20 S and 20 R configuration. The process is especially intended for the manufacture of alkaloids of the batrachotoxin type, particularly for batrachotoxinine A, which is a pregnane derivative having a 20 S alcohol grouping, and epimers and derivatives, such as epi-batrachotixinine A or 7,8-dihydrobatrachotoxinine A. The process is characterized by reducing the said $\Delta^{16}$-steroid-14β,18-diol-20-ones in form of their 14,18-ketals, for instance the 14,18 acetonides and using appropriate complex light metal hydrides and operating at appropriate temperatures. The separation of the two isomers is easy and can be effected by the usual physical operations, such as crystallization or chromatography. In the 14β,18,20-triols obtained the 18-hydroxy group can be dehydrogenated to the corresponding 18-aldehydes, which are intermediates necessary in the synthesis of the said pharmacological interesting substances, such as batrachotoxin, by treatment with a sulphoxide in the presence of a carboxylic acid anhydride.

11 Claims, No Drawings

PROCESS FOR THE MANUFACTURE OF $\Delta^{16}$-STEROID-14$\beta$,18,20-TRIOLS AND -14$\beta$,20-DIOL-18-OLS OF THE PREGNANE SERIES

CROSS REFERENCE TO RELATED APPLICATIONS

This is a continuation in part of application Ser. No. 364,466 filed on May 29, 1973 now abandoned which is a continuation in part of application Ser. No. 82 183 filed on Oct. 19, 1970.

The present invention relates to a process for the manufacture of $\Delta^{16}$-steroid-14$\beta$,18,20-triols and $\Delta^{16}$-steroid-14$\beta$,20-diol-18-als of the pregnane series and their esters and ethers, of which the 17-pregnane side chain has one of the two following partial formulae I 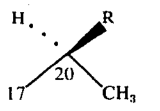 II 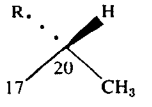

20 S configuration 20 R configuration wherein R represents a free, esterified or etherified hydroxyl group, from $\Delta^{16}$-steroid-14$\beta$,18-diol-20-ones of the pregnane series in which the 14,18-diol group is ketalised with a ketone.

The process can serve for the synthesis of pregnane derivatives which possess the abovementioned side chain in the 17-position and which possess pharmacologically interesting actions, and amongst these there are especially to be included the alkaloids of the batrachotoxin and batrachotoxinin A group.

Amongst the pregnane derivatives according to the present invention which have been mentioned, there are to be understood both compounds of the 5$\alpha$- and 5$\beta$-pregnane series and their derivatives which have a double bond starting from the 5-position.

Products of the process which are to be singled out particularly are those of the following formula III 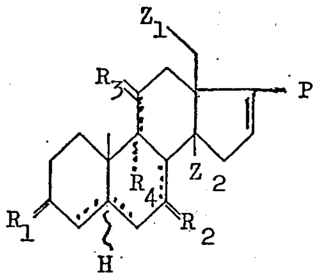

in which P has one of the abovementioned partial formulae I or II, $R_1$ denotes a free or protected oxo group or a free, esterified or etherified hydroxyl group together with a hydrogen atom, $R_2$ denotes two hydrogen atoms or a hydrogen atom next to a 7,8-double bond, a protected oxo group or a hydrogen atom together with a free, esterified or etherified hydroxyl group, $R_3$ denotes two hydrogen atoms or a hydrogen atom next to a 9,11-double bond or a free or protected oxo group or a free, esterified or etherified hydroxyl group together with a hydrogen atom, $R_4$ denotes a hydrogen atom or a free, esterified or etherified hydroxyl group and $R_1$ together with $R_4$ denotes a 3-hydroxy-3,9-oxido group or a 3-hydroxy-3,9-oxido group having the 3-hydroxy group in etherified or esterified form, and $Z_1$ and $Z_2$ each represent a free, esterified or etherified hydroxyl group and $Z_1$ and $Z_2$ together represent a ketalised 14,18-diol group and $Z_1$, however, also represents an oxo group, and in which double bonds can be present in one of positions 4,5 or 5,6 and/or in the case that $R_2$ or $R_3$ denotes a hydrogen atom, also in one of positions 7,8 and/or 9,11.

The esterified hydroxyl groups mentioned are preferably derived from organic carboxylic acids of the aliphatic, alicyclic, aromatic or heterocyclic series, especially from those with 1–18 carbon atoms, for example from lower aliphatic carboxylic acids with 1–6 C atoms, for example from formic acid, acetic acid, propionic acid, the butyric acids, valeric acids, such as n-valeric acid or trimethylacetic acid, trifluoroacetic acid, the caproic acids, such as $\beta$-trimethyl-propionic acid or diethylacetic acid or the oenanthic, caprylic, pelargonic or capric acids, undecylic acid, for example undecylenic acid, lauric, myristic, palmitic or stearic acids, for example oleic acid, cyclopropane-, -butane-, -pentane- and -hexane-carboxylic acid, cyclopropylmethanecarboxylic acid, cyclobutylmethanecarboxylic acid, cyclopentylethanecarboxylic acid, cyclohexylethanecarboxylic acid, cyclopentyl-, cyclohexyl- or phenyl-acetic acid or -propionic acids, benzoic acid, phenoxyalkanoic acids, such as phenoxyacetic acid, dicarboxylic acids, such as succinic acids, phthalic acid, quinolinic acid, furane-2-carboxylic acid, 6-tert.-butyl-furane-2-carboxylic acid, 5-bromo-furane-2-carboxylic acid, nicotinic acid or isonicotinic acid, or from pyrrolecarboxylic acids and alkyl-substituted pyrrolecarboxylic acids, such as 2,4,5-trimethylpyrrole-3-carboxylic acid, 2,4-dimethyl-pyrrole-3-carboxylic acid or 2-ethyl-4-methyl-pyrrole-3-carboxylic acid, or from sulphonic acids, such as benzenesulphonic acids or from inorganic acids such as, for example, phosphoric acids or sulphuric acids.

Etherified hydroxyl groups are preferably especially those which are derived from alcohols with 1–8 carbon atoms, such as lower aliphatic alkanols with 1–5 C atoms, such as ethyl alcohol, methyl alcohol, propyl alcohol, iso-propyl alcohol, butyl alcohols or amyl alcohols or from araliphatic alcohols, especially monocyclic aryl-lower aliphatic alcohols, such as benzyl alcohol, or from heterocyclic alcohols, such as $\alpha$-tetrahydropyranol or $\alpha$-tetrahydrofuranol.

The ether groups, and especially an etherified hydroxyl group in the 14-position can preferably also be derived from sulphur-containing alcohols, for example those of the formulae A) 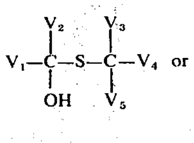 or B) 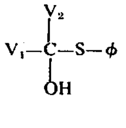

wherein $V_1$ – $V_5$ denote hydrogen or alkyl or aryl groups, especially lower alkyl groups, and $\phi$ denotes an aryl group, especially an unsubstituted or substituted phenyl nucleus, that is to say from 2-thiapropanols or 2-thia-arylethanols which are optionally substituted in the 1- and/or 3-position by further alkyl or aryl groups, above all from 2-thiapropanol. Such ether groups are formed, for example, on treating the hydroxy-steroid with dialkyl-sulphoxides or ar-alkyl-sulphoxides of the formula C) 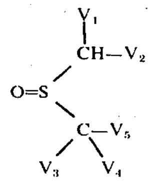 or D) 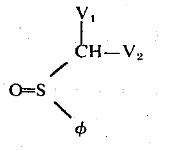

in the presence of a carboxylic acid anhydride, preferably of a lower aliphatic carboxylic acid anhydride.

Examples of protected oxo radicals are ketal groups, preferably those which are derived from lower alkanediols or alkanols, for example from ethylene glycol, methanol or ethanol.

A protected oxo group in the 3-position can in particular also be in the form of the 3-hydroxy-3,9-oxidohemiketal group or the form of the 3-ethers or 3-esters of such a hemiketal group, the ethers and esters being derived, for example, from the abovementioned alcohols or acids, preferably from lower aliphatic alcohols or acids. In particular, this hemiketal group is a 3α,9α-epoxy-3β-hydroxy group or its 3-ethers or 3-esters.

The compounds of the above formula III are valuable intermediate products in the manufacture of the pregnane compounds described, for example, in German Offenlegungsschriften No. 2,029,169, 2,052,166 and 2,136,635. Within the group of compounds encompassed by the formula III, compounds of the following formula are of great significance as important intermediate products for the manufacture of batrachotoxinin A, epibatrachotoxinin A and their 7,8-dihydro derivatives, as well as esters or ethers thereof, especially the 20-pyrrole carboxylic acid esters, which also include the known strongly active alkaloid batrachotoxin:

(IV) 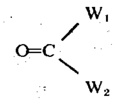

wherein P has the meaning indicated for the formula III, A denotes a hydroxyl group together with a hydrogen atom, or an oxo group, X denotes an etherified or esterified hydroxyl group, Y an esterified hydroxyl group, and Z denotes a hydrogen atom or an esterified hydroxyl group, as well as their esters and ethers and ketals of the 14,18-diols. The ester groups, amongst which there are especially also to be understood an esterified group R in the side chain P, are preferably in turn those from the abovementioned carboxylic acids or inorganic acids or sulphonic acids, especially the lower aliphatic carboxylic acids, above all acetic acid. The esterified hydroxyl groups are preferably derived from lower aliphatic alcohols with 1–5 C atoms or from one of the abovementioned heterocyclic alcohols, and especially also from the sulphur-containing alcohols mentioned, preferably from a 2-thiapropanol of the formula C) having up to 8 C atoms, such as, for example, 2-thiapropanol. The 14,18-ketals of 14,18-diols are above all those which are derived from a ketone of the formula (V) 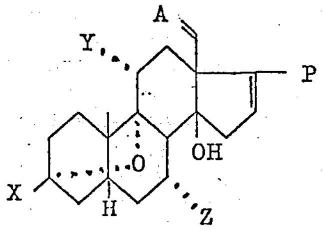

wherein $W_1$ and $W_2$ denote two unsubstituted or substituted hydrocarbon radicals or denote, together with the carbon atom to which they are bonded, an unsubstituted or substituted cyclised hydrocarbon radical. These groups $W_1$ and $W_2$ are above all aliphatic or araliphatic hydrocarbon radicals but can also be alicyclic or aromatic; they can optionally also be substituted, for example by hydroxyl, lower alkoxy, lower acyloxy, thiol or amino groups or halogen atoms, the term lower alkyl denoting groups with 1–6 carbon atoms. $W_1$ and $W_2$, together with the carbon atom to which they are bonded, can also form a cyclised hydrocarbon radical. Such a hydrocarbon radical is preferably an alicyclic hydrocarbon radical with a total of 1–12 C atoms and 5–7 ring carbon atoms, above all a cyclopentylidene or cyclohexylidene radical. If the groups $W_1$ and $W_2$ individually are hydrocarbon radicals of aliphatic nature, they preferably each possess 1–6 carbon atoms and are above all methyl, ethyl, propyl, butyl, pentyl or hexyl groups, but can also be of alicyclic nature such as, for example, cyclopentyl radicals or especially cyclohexyl radicals. Aromatic radicals $W_1$ and $W_2$ are in particular phenyl groups or phenyl groups substituted by lower alkyl radicals or halogen atoms.

Araliphatic groups $W_1$ and/or $W_2$ are especially those having the said alkyl groups of 1–6 C atoms and aromatic moiety are phenyl groups or the said substituted phenyl groups. Above all, $W_1$ and $W_2$ each represents a methyl group, that is to say the 14,18-diols which can be manufactured according to the present process are in the form of acetonides.

Amongst the compounds according to the above formula IV, an outstanding position is occupied by the compounds of the formulae (VI) 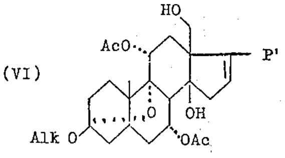 (VII) 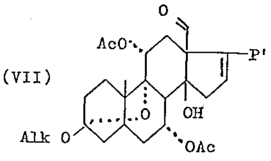

wherein Alk represents a lower alkyl group with 1–6 C atoms, Ac represents a lower aliphatic acyl radical with 1–6 C atoms and P' represents one of the two partial formulae (VIII) 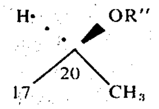

20 S configuration (IX) 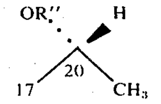

20 R configuration wherein R″ denotes hydrogen or a lower aliphatic acyl group with 1–6 C atoms, as well as the derivatives formed by ketalisation of the 14,18-diol grouping of the formula VI with the abovementioned preferred ketones of the formula V, and 14-ethers of the compounds of the formula VII, especially derived from one of the abovementioned alcohols, for example with one of the 2-thiapropanols, which have been mentioned, with 2–8 C atoms above all 2-thiapropanol. These compounds are particularly valuable for the synthesis of batrachotoxinin A and epi-batrachotoxinin A and their 20-esters, such as batrachotoxin. Specific compounds of this group are, for example, those of the formulae VI and VII wherein Alk denotes methyl and Ac denotes acetyl and R″ in the formulae VIII or IX denotes hydrogen or acetyl, the 14,18-acetonides in the case of the compounds of the formula VI, and the 14-(2′-thiapropyl)-ethers of the compounds of the formula VII.

The process of the present application for the manufacture of the $\Delta^{16}$-steroid-14β,18,20-triols and $\Delta^{16}$-steroid-14β,20-diol-18-als of the pregnane series and their esters and ethers is characterised in that a $\Delta^{16}$-20-oxo-steroid-14β,18-diol of the pregnane series, in which the 14,18-diol group is ketalised with a ketone, is treated with a complex light metal hydride which reduces an oxo group to the hydroxyl group, but which leaves esterified hydroxyl groups intact, and, if desired, in optional sequence and optionally simultaneously, at least one of the two epimers is isolated in a manner which is in itself known from the mixture of the 20 S and 20 R hydroxy compounds formed, or their functional derivatives, and/or protected functional groups which may be present are liberated and/or functional groups are functionally modified and/or the 18-hydroxyl group is selectively dehydrogenated to the 18-oxo group.

The reduction, according to the process, of the starting substances which have been characterised is carried out with complex hydrides which leave esterified hydroxyl groups intact. As such it is possible to use, above all, alkali metal borohydrides, especially sodium borohydride, and complex alkali metal-aluminium hydrides of the type

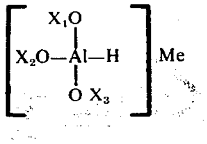

(X)

wherein $X_1$, $X_2$ and $X_3$ each denote a tertiary lower alkyl group and Me denotes an alkali metal, such as, for example, tri-tert. butoxy-lithium-aluminium hydride or tri-tert. amyloxy-lithium-aluminium hydride. The reduction with these complex hydrides is carried out in a manner which is in itself known. The solvents used are, for example, in the case of the complex alkali metal -aluminium hydrides mentioned, an ether, such as diethyl ether, diisopropyl ether, dioxane or tetrahydrofurane, and in the case of an alkali metal borohydride preferably an aliphatic or cycloaliphatic alcohol such as, for example, methanol, ethanol, propyl alcohol, isopropyl alcohol, the butanols or amyl alcohols.

The temperature for carrying out the reduction according to the process can vary within the wide limits, the ratio of the two 20-epimeric alcohols formed in the reaction mixture varying depending on the temperature chosen. It is possible, especially in the case that alkali metal borohydrides are used, to work at low temperatures, for example 0° to −50°, but also below, or especially in the case that tri-tert. alkoxy-lithium-aluminium hydrides are used, to work above 0°, for example between 0° and 100°. The reaction time to be chosen depends on the starting product used, on the reducing agent and on the reaction temperature; in general it is several hours.

The isolation of at least one of the epimeric 20-hydroxy compounds from the reaction mixture can be carried out before or after the liberation of functional groups, especially of the 14,18-ketal grouping present in the reduction product, and before or after functional conversion of other groups, such as especially the 20-alcohol group. The isolation can be achieved in a manner which is in itself known, by crystallisation, chromatography or other physical or chemical methods.

If desired it is possible, in optional sequence, to convert protected functional groups, such as, for example, ketal, ether or ester groups, into the corresponding free functional groups, and this can be done in a manner which is in itself known. Thus, for example, ketalised oxo groups or the ketalised 14,18-diol group and ether groups are preferably split by the action of acid agents such as mineral acids, for example hydrochloric acid, sulphuric acid or perchloric acid, or organic carboxylic acids and sulphonic acids such as, for example, lower aliphatic carboxylic acids, for example acetic acid, whilst ester groups are preferably split by the action of basic agents. Thus, for example, the 14,18-ketal grouping is preferably saponified to the 14,18-diol group by the action of a strong acid such as p-toluenesulphonic acid.

The functional modification of hydroxyl groups or oxo groups can also be carried out in a manner which is in itself known. The esterification of free hydroxyl groups can be achieved, for example, by treatment with an acylating derivative of an acid, such as of a carboxylic acid, preferably the anhydride or a halide, for example in the presence of a tertiary base, such as pyridine or collidine.

The etherification of free hydroxyl groups is carried out, for example, by treatment with a reactive functional derivative of the alcohol in question, such as an alkyl halide or alkyl sulphate, for example a dialkyl sulphate, in the presence of an organic or inorganic base such as sodium hydroxide or potassium hydroxide or pyridine.

The isolation of the 20 R- and 20 S-hydroxy compounds is preferably carried out on the mixture of the free alcohols obtained directly by reduction with the complex light metal hydride. However, if desired the isolation can be carried out at a later stage, for example after esterification of free hydroxyl groups, especially of the 20-hydroxyl group itself, that is to say the epimeric 20-hydroxy compounds can also be isolated in the form of one of their functional derivatives.

If compounds with a free 14,18-diol group or with an 18-aldehyde group are to be manufactured, the 14,18-ketal group is removed at any desired stage in a manner which is in itself known, for example as described above. Preferably, this is done after separating the epimer mixture of the 20-alcohols and, especially if the 18-hydroxyl group is subsequently to be dehydrogenated to the oxo group, after esterification of oxidisable free hydroxyl groups, for example of the 20-hydroxyl group.

The selective dehydrogenation of the 18-hydroxyl group to the oxo group, which can optionally be carried out according to the present process, is preferably carried out after prior protection of oxidisable free hydroxyl groups in other positions, for example after acylation of a 20-hydroxyl group. The oxidising agents used are those known from the literature for the dehydrogenation of a primary alcohol to the aldehyde group, such as, for example, compounds of hexavalent chromium, for example chromium trioxide, especially chromium trioxide in pyridine, optionally with the addition of other solvents, such as chlorinated hydrocarbons, for example methylene chloride, or chromium trioxide in acetone and sulphuric acid (Jones reagent) or chromium trioxide and pyridine-sulphur trioxide complex. A particularly advantageous method which gives good yields is the oxidation with dimethylsulphoxide-acetic anhydride according to the method of Albright and Goldmann (Journal of the American Chemical Society 89, 2416 (1967)). It is also possible to use similar mixtures of a homologue of dimethylsulphoxide, such as those mentioned above, of the formulae C) and D), and of acetic anhydride, such as diethylsulphoxide and propionic anhydride. When using this method, the 18-hydroxyl group is dehydrogenated to the aldehyde group and simultaneously the 14-hydroxyl group is etherified with the thiapropanol of the above general formulae A) or B) corresponding to the dialkylsulphoxide in question. When using dimethylsulphoxide, for example, the 14-hydroxyl group is converted into the 2-thiapropoxy group (or methyl-thio-methoxy group) $—O — CH_2 — S — CH_3$. The 14-hydroxyl group etherified in this way can easily be hydrolysed, even under mild conditions, to the alcohol by acid treatment or by treatment with chloramine in dioxanewater. If the acid treatment is carried out, for example, with hydrochloric acid in an alcohol, the corresponding acetal of the 18-aldehyde group is formed simultaneously.

The 14-ethers, which have been mentioned, of the 18-aldehydes formed are particularly valuable starting products or intermediate products for the manufacture of batrachotoxinin A and epi-batrachotoxinin A compounds and of their analogues and conversion products, as is shown later.

The 14,18-ketals of $\Delta^{16}$-20-oxo-steroid-14$\beta$,18-diols of the pregnane series, which are to be used as starting substances, can be manufactured in a manner which is in itself known by reaction of the corresponding 14$\beta$,18-diols with the desired ketone or, even more advantageously, with a ketal of such a ketone, with addition of an acid agent, preferably in catalytic amounts. The ketals used are preferably lower aliphatic ketals of the ketone, above all the dimethylketals, for example 2,2-dimethoxypropane in the case of acetone, and the reaction is preferably carried out at room temperature, in the presence of traces of an acid, for example p-toluenesulphonic acid.

The $\Delta^{16}$-20-oxo-steroid-14$\beta$,18-diols of the pregnane series which have been mentioned are known or can be manufactured according to published methods. In particular, those starting substances are used which possess the substituents specified above or correspond to the abovementioned formulae III – VII of the process products. The manufacture of such starting substances is described, for example, in German Offenlegungsschrift No. 2,136,635.

A preferred combination of the process steps described is that after the reduction of the 14,18-ketals of the $\Delta^{16}$-20-oxo-steroid-14$\beta$,18-diols with the complex light metal hydrides mentioned, the 20-hydroxyl group is acylated, in the manner described above, in the corresponding $\Delta^{16}$-20-hydroxy compounds obtaind, the 14,18-ketal group in the resulting compounds is split by the action of an acid under mild conditions, as explained above, and the 18-hydroxyl group is dehydrogenated according to the abovementioned method of Albright and Goldmann, using a lower aliphatic dialkylsulphide in the presence of a lower aliphatic carboxylic acid anhydride, whereby the $\Delta^{16}$-20-acyloxy-14$\beta$-(2'-thialkoxy)-18-als are formed, and, if desired, at least one of the epimeric 20 R-OH or R-O-Ac and 20 S-OH or S-O-Ac compounds formed is isolated at any desired stage. Preferably, the isolation of the compounds which are epimeric in the 20-position is carried out immediately after the reduction stage, on the free alcohols. This combination is illustrated by the following reaction scheme in the case of a starting compound corresponding to the compounds of the above formula VI

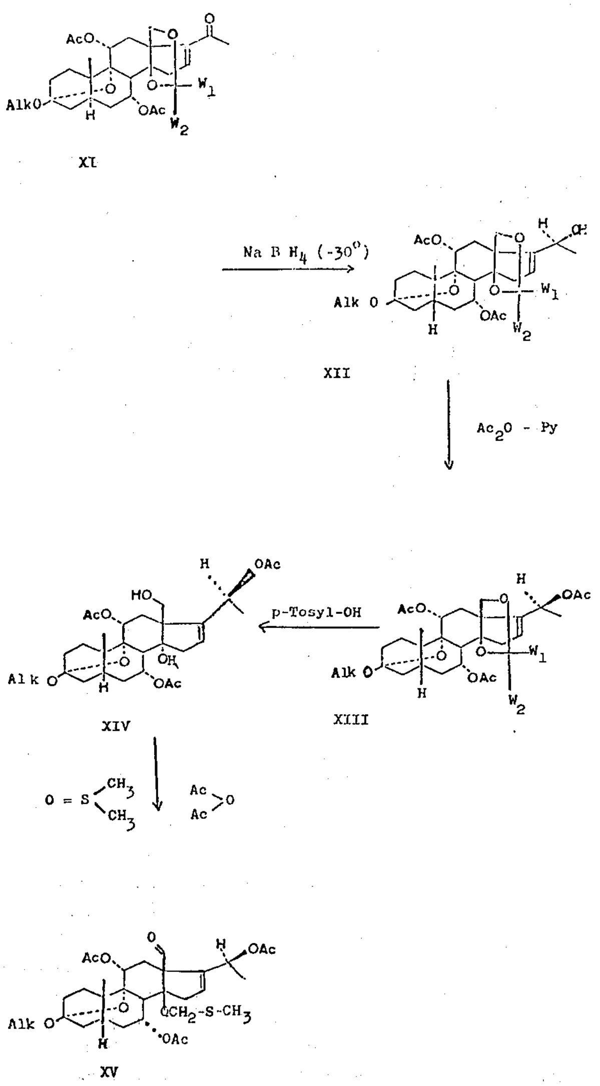

In this scheme, Alk denotes a lower alkyl group, above all methyl, and Ac denotes a lower aliphatic acyl radical, above all acetyl, whilst $W_1$ and $W_2$ have the meaning indicated for the above formula V. The splitting of the ketal group is carried out under mild conditions, for example by means of catalytic amounts of an acid at room temperature and using a short reaction time; under these conditions, an etherified hemiketal group, such as the etherified 3α,9α-hemiketal group shown above, remains unattacked.

In the above scheme, the reduction is carried out with $NaBH_4$ at a low temperature in methanol, whereupon the 20 S-OH-epimer is formed predominantly, and this can, without difficulties, be isolated from the reaction product, for example by simple crystallisation. According to the special combination of process steps described above it is possible, by varying the reaction conditions and the reducing agents, to obtain mixtures of the two epimeric 20-pregnane-alcohols in varying ratios, and the pure epimers are optionally isolated at any desired stage. When using, for example, the abovementioned hydrides of the formula X at an elevated temperature, for example at 70°, the 20 R-alcohol is predominantly obtained and this can also be isolated easily from the reaction product.

The conversion of the products of the process into the initially mentioned pharmacologically active compounds can be illustrated by means of the following reaction scheme, which shows the conversion of a compound of the above formula XV into batrachotoxinin A:

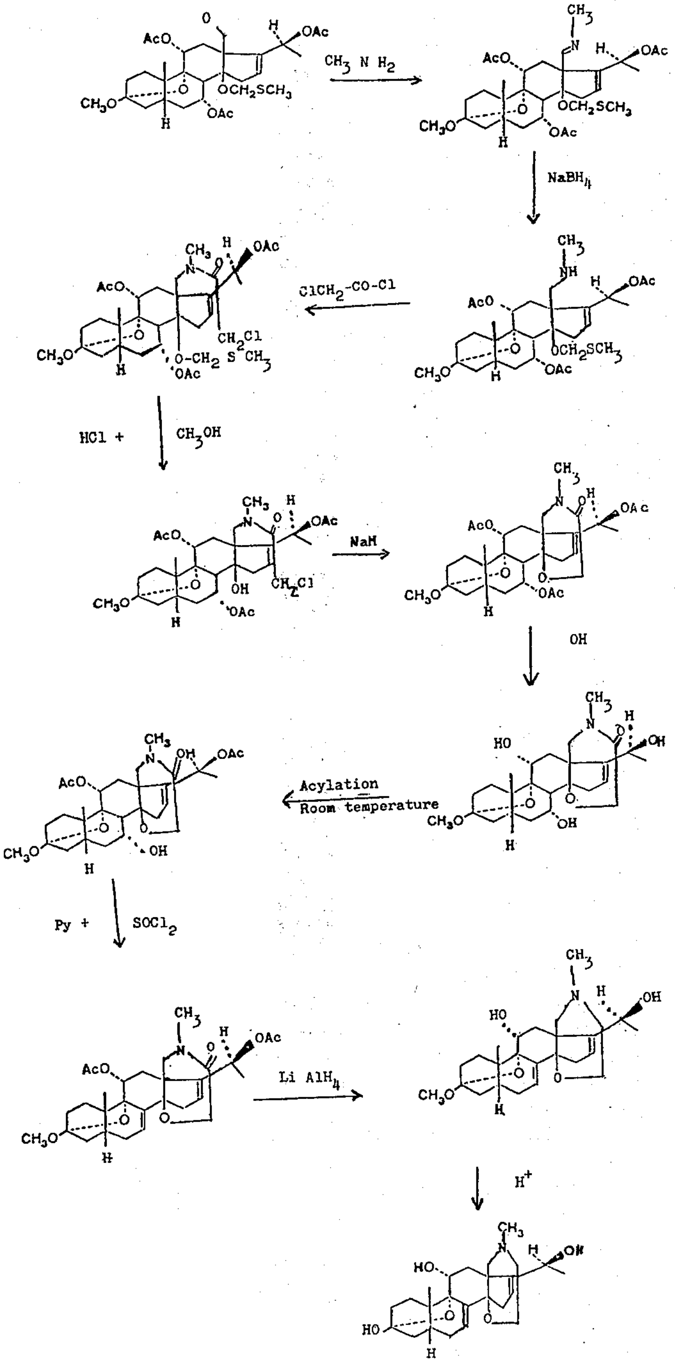

Batrachotoxinin A

Analogously, 20 S-and 20 R-epimers of, for example, the compounds described in the abovementioned German Offenlegungsschrift 2,052,166 can be prepared from corresponding process products of the present invention.

The invention is described in the examples which follow. The optical rotations are measured in chloroform (temperature 22°C), the IR spectral data are given as wave numbers ($cm^{-1}$), the measurement again being carried out in chloroform, and the UV-spectral data relate to the measurement in ethanol, the figures indicated in each case showing the wavelength $\lambda_{max}$, expressed in nanometres, and extinction values $\epsilon$, corresponding to the maximum absorption.

Unless expressly noted otherwise, "working-up" of a reaction mixture obtained denotes taking up the reaction mixture in ethyl acetate, washing the mixture with water or saturated sodium chloride solution until it is neutral, drying over magnesium sulphate and evaporating in a rotary evaporator. Unless otherwise noted, chromatography involves the use of highest purity silica gel, 0.05–0.2 mm, from Merck, and "crystallisation" or "crystallising" means dissolving in, and separating out from, acetone-hexane or ether-hexane.

EXAMPLE 1

2 g of 3β-methoxy-3α,9α-oxido-11α-acetoxy-14β,18-dihydroxy-20-oxo-$\Delta^{16}$-5β-pregnene and 60 mg of p-toluenesulphonic acid in 80 ml of 2,2-dimethoxypropane are stirred for 20 minutes. The mixture is then neutralised with aqueous sodium bicarbonate solution and worked-up. A single crystallisation of the crude product, and chromatography of the mother liquor, resulting therefrom, in benzene-ethyl acetate (1:1) solution, yields a total of 1.9 g of the (14β → 18)-acetonide of 3β-methoxy-3α,9α-oxido-11α-acetoxy-14β,18-dihydroxy-20-oxo-$\Delta^{16}$-5β-pregnene, melting point 183°–184°C. $[\alpha]_D$ = –47° (0.38). IR: 1,730, 1,665, 1,615, 1,370 (strong) and 1,240. UV 239 (8,300 ).

EXAMPLE 2

316 mg of the (14 → 18)-acetonide of 3β-methoxy-3α,9α-oxido-11α-acetoxy-14β,18-dihydroxy-20-oxo-$\Delta^{16}$-5β-pregnene in 15 ml of absolute dioxane are reduced with 700 mg of tritert.butoxy-lithium-aluminium hydride for 15 minutes at 70°C. Customary working-up, and chromatography in methylene chloride-methanol (20:1) mixture, first yield 142 mg of crystalline (14 → 18)-acetonide of (20R)-3β-methoxy-3α,-9α-oxido-11α-acetoxy-14β,18,20-trihydroxy-$\Delta^{16}$-5β-pregnene. Melting point, after three crystallisations, 141°–143°C. IR: 3,500 (broad), 2,830, 1,740 and 1,250.

Later fractions yield 64 mg of amorphous (14 → 18)-acetonide of (20S)-3β-methoxy-3α,9α-oxido-11α-acetoxy-14β,18,20-trihydroxy-$\Delta^{16}$-5β-pregnene. IR: 3,600, 3,500 (broad), 2,830, 1,738 and 1,240.

EXAMPLE 3

400 mg of the (14 → 18)-acetonide of 3β-methoxy-3α,9α-oxido-11α-acetoxy-14β,18-dihydroxy-20-oxo-$\Delta^{16}$-5β-pregnene are reduced, in 30 ml of absolute dioxane, with 1.2 g of tri-tert.amyloxy-lithium-aluminium hydride for 20 minutes at 80°C. Working-up, and chromatography in methylene chloride-methanol (50:1) solution yield 213 mg of the (14 → 18)-acetonide of (20R)-3β-methoxy-3α,9α-oxido-11α-acetoxy-14β,18,20-trihydroxy-$\Delta^{16}$-5β-pregnene and 77 mg of the (14 → 18)-acetonide of (20S)-3β-methoxy-3α,9α-oxido-11α-acetoxy-14β,18,20-trihydroxy-$\Delta^{16}$-5β-pregnene.

EXAMPLE 4

700 mg of the (14 → 18)-acetonide of 3β-methoxy-3α,9α-oxido-11α-acetoxy-14β,18-dihydroxy-20-oxo-$\Delta^{16}$-5β-pregnene, dissolved in 50 ml of absolute methanol, are cooled to –30°C and 500 mg of solid sodium borohydride are added. The mixture is then stirred for 19 minutes at –30°C and is worked-up and chromatographed in methylene chloride-methanol (50:1) solution. Herein, 121 mg of the (14 → 18)-acetonide of (20R)-3β-methoxy-3α,9α-oxido-11α-acetoxy-14β, 18,20-trihydroxy-$\Delta^{16}$-5β-pregnene are eluted first. Later fractions yield 462 mg of the corresponding (20S)-epimer.

EXAMPLE 5

331 mg of the (14 → 18)-acetonide of (20R)-3β-methoxy-3α,9α-oxido-11α-acetoxy-14β,18,20-trihydroxy-$\Delta^{16}$-5β-pregnene are acetylated in 40 ml of acetic anhydridepyridine (1:1) mixture overnight at room temperature. The reaction mixture is then evaporated in vacuo and the crude product, in methylene chloride, is filtered over neutral aluminium oxide (activity III). This yields 320 mg of amorphous (14 → 18)-acetonide of (20R)-3β-methoxy-3α,9α-oxido-11α,20-diacetoxy-14β,18-dihydroxy-$\Delta^{16}$-5β-pregnene. IR: 1,730 and 1,240.

EXAMPLE 6

495 mg of the (14 → 18)-acetonide of (20S)-3β-methoxy-3α,9α-oxido-11α-acetoxy-14β,18,20-trihydroxy-$\Delta^{16}$-5β-pregnene are acetylated as in the preceding example. This yields 501 mg of amorphous (14 → 18)-acetonide of (20S)-3β-methoxy-3α,9α-oxido-11β,20-diacetoxy-14β,18-dihydroxy-$\Delta^{16}$-5β-pregnene. IR: 1,730 and 1,240.

EXAMPLE 7

330 mg of the (14 → 18)-acetonide of (20R)-3β-methoxy-3α,9α-oxido-11α,20-diacetoxy-14β,18-dihydroxy-$\Delta^{16}$-5β-pregnene are dissolved in 40 ml of methanol and a solution of 40 mg of p-toluenesulphonic acid in a mixture of 20 ml of methanol and 4 ml of water is added. The reaction mixture is then left to stand at room temperature for ¾ hours and is subsequently worked-up. This yields 280 mg of (20R)-3β-methoxy-3α,9α-oxido-11α,20-diacetoxy-14β,18-dihydroxy-$\Delta^{16}$-5β-pregnene, which are not purified. IR: 3,550 (broad), 3,400 (broad), 1,730 and 1,250.

EXAMPLE 8

530 mg of the (14 → 18)-acetonide of (20S)-3β-methoxy-3α,9α-oxido-11α,20-diacetoxy-14β,18-dihydroxy-Δ[16]-5β-pregnene, in 35 ml of absolute methanol, are left to stand with 15 mg of p-toluenesulphonic acid for 15 minutes at room temperature. Working-up, and one crystallisation of the crude product from methylene chloride-hexane, yield 398 mg of crystals of (20S)-3β-methoxy-3α,9α-oxido-11α,20-diacetoxy-14β,18-dihydroxy-Δ[16]-5β-pregnene of melting point 175°-176°C. $[\alpha]_D$=−1° (0.65). IR: 3,520, 3,400, 1,725 and 1,250.

EXAMPLE 9

260 mg of (20R)-3β-methoxy-3α,9α-oxido-11α,20-diacetoxy-14β,18-dihydroxy-Δ[16]-5β-pregnene are dissolved in 6 ml of absolute dimethylsulphoxide, 6 ml of absolute acetic anhydride are added and the mixture is left to stand for 17 hours at room temperature. It is then worked-up and the resulting crude product is chromatographed in a benzene-ethyl acetate (4:1) mixture. This yields 220 mg of (20R)-3β-methoxy-3α,9α-oxido-11α,20-diacetoxy-14β-methyl-thiomethoxy-18-oxo-Δ[16]-5β-pregnene in the amorphous form. IR: 2,750, 1,735 and 1,245.

EXAMPLE 10

298 mg of (20S)-3β-methoxy-3α,9α-oxido-11α,20-diacetoxy-14β,18-dihydroxy-Δ[16]-5β-pregnene are reacted in 9 ml of dimethylsulphoxide-acetic anhydride (1:1) mixture, as in the preceding example, and the product is then worked-up and chromatographed in benzene-ethyl acetate (2:1) solution. This yields 255 mg of crystals of (20S)-3β-methoxy-3α,9α-oxido-11α,20-diacetoxy-14β-methyl-thiomethoxy-18-oxo-Δ[16]-5β-pregnene of melting point 114°-115°C. $[\alpha]_D$=+24 (0.75). IR: 2,830, 2,740, 1,735 and 1,245.

EXAMPLE 11

120 mg of 3β-methoxy-3α,9α-oxido-7α,11α-diacetoxy-14β,18-dihydroxy-20-oxo-Δ[16]-5β-pregnene and 3 mg of p-toluenesulphonic acid in 3 ml of 2,2-dimethoxypropane are stirred for 10 minutes at room temperature. The mixture is then added to aqueous $NaHCO_3$ solution, the whole is extracted with ethyl acetate and the extract is washed with saturated aqueous NaCl solution until neutral. The crude product obtained after drying and evaporation of the organic phase is chromatographed, in benzene-ethyl acetate (1:1) solution, on silica gel. This yields 100 mg of crystals of the (14 → 18)-acetonide of 3β-methoxy-3α,9α-oxido-7α,11α-diacetoxy-14β,18-dihydroxy-20-oxo-Δ[16]-5β-pregnene (melting point 194°-195°C after one recrystallisation). $[\alpha]_D$ = − 65° (0.60), IR: 1,730, 1,665, 1,620 and 1,240. UV: 236 (9,580).

EXAMPLE 12

40 mg of the (14 → 18)-acetonide of 3β-methoxy-3α,9α-oxido-7α,11α-diacetoxy-14β,18-dihydroxy-20-oxo-Δ[16]-5β-pregnene, in 3 ml of absolute dioxane, are reduced with 160 mg of Li[Al(t-amyloxy)$_3$H] for 15 minutes at 80°C. The mixture is then added to saturated aqueous $(NH_4)_2SO_4$ solution, the whole is extracted with ethyl acetate and the extract is subsequently washed with saturated aqueous NaCl solution until neutral. After drying and evaporation of the organic phase, 40 mg of crude product result, and are chromatographed, in methylene chloride-methanol (100:1) solution, on silica gel. First, 23 mg of (14 → 18)-acetonide of (20R)-3β-methoxy-3α,9α-oxido-7α,11α-diacetoxy-14β,18,20-trihydroxy-Δ[16]-5β-pregnene are eluted, melting at 206–207°C after one crystallisation. $[\alpha]_D$ = − 33° (0.45). IR: 3,460 (broad), 1,730 and 1,240.

Later fractions yield 7 mg of (14 → 18)-acetonide of (20S)-3β-methoxy-3α,9α-oxido-7α,11α-diacetoxy-14β,18,20-trihydroxy-Δ[16]-5β-pregnene, melting at 160°-161°C after crystallisation. $[\alpha]_D$ = − 36° (0.50). IR: 3,590, 3,450 (broad), 1,730 and 1,240.

200 mg of the starting material used, in 15 ml of absolute methanol, are treated with 200 mg of solid $NaBH_4$ at −30°C. The mixture is then left at −30°C for 24 hours whilst stirring, a further 100 mg of $NaBH_4$ being added after 5 hours. The whole is then diluted with ethyl acetate and washed with saturated aqueous NaCl solution until neutral. After drying and evaporation of the organic phase, the residue is chromatographed as above. First, 50 mg of the (20R) compound described above are eluted. Later fractions yield 120 mg of the (20S) compound described above.

EXAMPLE 13

120 mg of (14 → 18)-acetonide of (20S)-3β-methoxy-3α,9α-oxido-7α,11α-diacetoxy-14β,18,20-trihydroxyΔ[16]-5β-pregnene are acetylated in 5 ml of acetic anhydridepyridine (1:1) mixture for 3 hours at room temperature. The mixture is then evaporated in vacuo, which yields 125 mg of (14 → 18)-acetonide of (20S)-3β-methoxy-3α,9α-oxido-7α,11α,20-triacetoxy-14β,18-dihydroxy-Δ[16]-5β-pregnene (IR: 1,730 and 1,240), which are reacted, without purification, in 6 ml of absolute methanol with a solution of 6 mg of p-toluenesulphonic acid in a further 6 ml of absolute methanol for 15 minutes at room temperature. The mixture is then diluted with ethyl acetate, washed with saturated aqueous NaCl solution until neutral and evaporated in vacuo and the crude product (115 mg) is crystallised from etherhexane. (20S)-3β-Methoxy-3α,9α-oxido-7α,11α,20-triacetoxy-14β,18-dihydroxy-Δ[16]-5β-pregnene of melting point 172°-173°C is thus obtained. $[\alpha]_D$ = + 48° (0.35), IR: 3,580, 3,460 (broad), 1,730 and 1,240.

EXAMPLE 14

160 mg of (20S)-3β-methoxy-3α,9α-oxido-7α,11α,20-triacetoxy-14β,18-dihydroxy-Δ[16]-5β-pregnene are dissolved in 3 ml of absolute dimethylsulphoxide, 3 ml of absolute acetic anhydride are added and the mixture is left overnight at room temperature. It is then added to ice-cold aqueous $NaHCO_3$ solution, the whole is extracted with ethyl acetate and the extract is washed with a large amount of water until neutral. The crude product obtained after drying and evaporation of the organic phase is chromatographed, in benzene-ethyl acetate (3:1) solution, on silica gel. This yields 130 mg of crystals of (20S)-3β-methoxy-3α,9α-oxido-7α,11α,20-triacetoxy-14β,0-methyl-thiomethoxy-18-oxo-Δ[16]-5β-pregnene, melting at 125°-126°C after crystallisation. $[\alpha]_D$=+25° (0.40). IR: 2,740, 1,730 and 1,240.

EXAMPLE 15

The starting substance of Example 11 can be obtained as follows:

720 mg of 3β-methoxy-3α,9α-oxido-7α-hydroxy-11α,18-diacetoxy-20-oxo-5β-pregnane [Helv. 54. 2,879 (1971)] are acetylated in 30 ml of acetic anhydride-pyridine (1:1) mixture under a $N_2$ atmosphere for 6 hours at 130°C. The reaction mixture is then evaporated in vacuo and the residue, in ethyl acetate-chloroform (1:1) solution, is chromatographed on silica gel. This yields 470 mg of 3β-methoxy-3α,9α-oxido-7α,11α,18-triacetoxy-20-oxo-5β-pregnane, which after one recrystallisation melt at 146°–147°C. $[\alpha]_D = +81°$ (0.64). IR: 1,735, 1,710 and 1,245.

470 mg of 3β-methoxy-3α,9α-oxido-7α,11α,18-triacetoxy-20-oxo-5β-pregnane in 40 ml of $CCl_4$ are boiled with 200 mg of N-bromosuccinimide, with addition of 10 mg of azobisisobutyronitrile, for 45 minutes whilst irradiating externally with a 1000 W incandescent lamp. The succinimide which has precipitated is then filtered off and the filtrate is evaporated in vacuo. The resulting crude bromination product is dissolved in 40 ml of absolute dimethylformamide and warmed, with 470 mg of LiBr and 470 mg of $Li_2CO_3$, to 130°C over the course of 2½ hours, under $N_2$. The mixture is then concentrated in vacuo, diluted with ethyl acetate and repeatedly washed with water. The crude product resulting after drying and evaporation of the organic phase is chromatographed, in ethyl acetate-chloroform (1:1) mixture, on silica gel. This yields 265 mg of crystals of 3β-methoxy-3α,9α-oxido-7α,11α,18-triacetoxy-20-oxo-$\Delta^{16}$-5β-pregnene, which after one recrystallisation melt at 187°–188°C. $[\alpha]_D = +53°$ (0.54). IR: 1,730, 1,670, 1,595, and 1,240; UV. 235 (8,550).

265 mg of the product thus obtained and 110 mg of N-bromosuccinimide as well as 10 mg of azobisisobutyronitrile, in 40ml of $CCl_4$, are boiled for 20 minutes under external irradiation from a 1,000 W incandescent lamp. The mixture is then cooled, freed of the precipitated succinimide by filtration, and evaporated in vacuo. The crude bromination product is warmed under $N_2$ with 265 mg of LiBr and 265 mg of $Li_2CO_3$ in 20 ml of absolute dimethylformamide to 130°C for 15 minutes. The mixture is then evaporated in vacuo, the residue is taken up in ethyl acetate and the solution is repeatedly washed with water. The crude product which is obtained after evaporation in vacuo is chromatographed, in benzene-ethyl acetate (1:1) solution, on silica gel. This yields 185 mg of crystals of 3β-methoxy-3α,9α-oxido-7α,11α,18-triacetoxy-20-oxo-$\Delta^{14,16}$-5β-pregnadiene, which after one recrystallisation melt at 209°C. $[\alpha]_D = +227°$ (0.60). IR: 1,735, 1,640, 1,530, 1,465 and 1,240. UV: 309 (10,900).

187 g of the product thus obtained, in 18 ml of $CHCl_3$-methanol (100:1) mixture, are epoxidised with 185 mg of p-nitroperbenzoic acid for 24 hours at room temperature, in the dark. The mixture is then diluted with ethyl acetate and is washed successively with aqueous solutions of NaI,$Na_2S_2O_3$,NaCl, $NaHCO_3$ and again NaCl. It is then dried over $MgSO_4$ and evaporated in vacuo and the residue, in ethyl acetate-chloroform (1:1) solution, is chromatographed on silica gel. 109 mg of crystals of 3β-methoxy-3α,9α;14β,15β-dioxido-7α,11α,18-triacetoxy-20-oxo-$\Delta^{16}$-5β-pregnene are eluted, melting at 199°–200°C after one recrystallisation. $[\alpha]_D = +33°$ (0.65). IR: 1,735, 1,670, 1,605 and 1,250. UV: 244 (7,850).

250 mg of the product thus obtained in a mixture of 28 ml of methanol and 2 ml of cyclohexene are boiled, in the presence of 375 mg of 5 per cent strength Pd-$BaSO_4$ catalyst, for 3 hours with vigorous stirring, at an oil bath temperature of 120°C. The catalyst is then removed by filtration through Celite, the filtrate is evaporated in vacuo and the residue, in a benzene-methanol (40:1) mixture, is chromatographed on silica gel. This yields 155 mg of 3β-methoxy-3α,9α-oxido-7α,11α,18-triacetoxy-14β-hydroxy-20-oxo-$\Delta^{16}$-5β-pregnene in the amorphous form. IR: 3,580, 1,735, 1,670, 1,615 and 1,250. UV: 836 (9,860).

205 mg of the product thus obtained, in 20 ml of 0.1 N $NaHCO_3$ in 90 per cent strength aqueous methanol, are boiled for 15 minutes under $N_2$ (oil bath temperature 80°C). The mixture is then diluted with ethyl acetate, washed with saturated aqueous NaCl solution until neutral and evaporated in vacuo, and the residue, in ethyl acetate, is chromatographed on silica gel. This yields 140 mg of crystals of 3β-methoxy-3α,9α-oxido-7α,11α-diacetoxy-14β,18-dihydroxy-20-oxo-$\Delta^{16}$-5β-pregnene, which melt at 222°C after two crystallisations. $[\alpha]_D = -41°$ (0.50). IR: 3,600, 3,450, 1,730, 1,655, 1,610 and 1,240. UV: 236 (9,960).

EXAMPLE 16

The conversion of the product obtained in Example 14 into batrachotoxinin A is carried out as follows:

220 mg of (20S)-3β-methoxy-3α,9α-oxido-7α,11α,20-triacetoxy-14β-methyl-thiomethoxy-18-oxo-$\Delta^{16}$-5β-pregnene are dissolved in 4 ml of absolute benzene and warmed, together with 1.5 ml of a saturated solution of methylamine in benzene, for 9 hours to 85°C in a bomb tube. The mixture is then cooled and evaporated in vacuo. This yields 220 mg of (20S)-3β-methoxy-3α,9α-oxido-7α,11α,20-triacetoxy-14β-methyl-thiomethoxy-18methylimino-$\Delta^{16}$-5β-pregnene (IR: 2,770, 1,730, 1,665 and 1,240), which are reduced, without purification, in 18 ml of methanol, at room temperature, with 220 mg of $NaBH_4$ in 2 ml of water, over the course of 10 minutes. The mixture is then diluted with ethyl acetate, washed with saturated aqueous NaCl solution until neutral, dried over $MgSO_4$ and evaporated in vacuo. This yields 210 mg of (20S)-3β-methoxy-3α ,9α-oxido-7α,11α,20-triacetoxy-14β0-methyl-thiomethoxy-18-methylamino-$\Delta^{16}$-5β-pregnene (IR: 3,340, 2,800, 1,730 and 1,240), which are again treated successively, without purification, in 20 ml of alcohol-free chloroform, at 0°C, with 1.5 ml of chloroacetyl chloride and 0.28 g of NaOH in 20 ml of water. The two-phase system is then left for 15 minutes at 0°C whilst stirring vigorously and is subsequently poured onto saturated aqueous $NaHCO_3$ solution, the mixture is extracted with ethyl acetate and the extract is washed with saturated aqueous NaCl solution until it is neutral. After drying and subsequent evaporation of the organic phase, 220 mg of (20S)-3β-methoxy-3α,9α-oxido-7α,11α,20-triacetoxy-14β-methyl-thiomethoxy-18-(N-methyl-N-chloroacetyl-amino)-$\Delta^{16}$-5β-pregnene are obtained, which are left, without prior purification and characterisation, for 1¾ hours at room temperature in 10 ml of an 0.05 N HCl solution in absolute methanol. This mixture is then poured into aqueous $NaHCO_3$ solution, the mixture is extracted with ethyl acetate and the extract is washed with saturated aqueous NaCl solution until neutral. The crude product obtained after drying and evaporation of the organic phase is subsequently chromatographed, in benzene-ethyl acetate (1:1) solution on silica gel. This yields 150 mg of crystals of (20S)-3β-methoxy-3α,9α-oxido-7α,11α,20-triacetoxy-14β-hydroxy-18-(N-methyl-N-chloroacetyl-amino)-$\Delta^{16}$-5β-pregnene, the melting point of which after one crystallisation is 203°–204°C. [ $\alpha]_D$ = +39° (0.40). IR: 3,350 (broad), 1,730, 1,645 and 1,245.

170 mg of NaH dispersion are freed of adhering mineral oil by washing four times with absolute pentane. The material is then covered with 5 ml of absolute benzene and 80 mg of (20S)-3β-methoxy-3α,9α-oxido-7α,11α,20-triacetoxy-14β-hydroxy-18-(N-methyl-N-chloroacetyl-amino)-$\Delta^{16}$-5β-pregnene in 5 ml of absolute tetrahydrofurane are added under argon. Finally, one drop of a solution of 20 mg of ethanol in 10 ml of absolute benzene is also added and the mixture is boiled under argon, and whilst stirring, for 2 hours. 0.4 ml of methanol is then added and the mixture is boiled for a further hour in order to hydrolyse the acetate groupings on C-7, C-11 and C-20. It is then poured onto saturated aqueous $(NH_4)_2SO_4$ solution, the mixture is extracted with ethyl acetate, and the organic phase is washed with saturated aqueous NaCl solution until neutral, dried and evaporated in vacuo. This yields 50 mg of crude (20S)-3β-methoxy-3α,9α-oxido-7α,11α,20-trihydroxy-14β0, 18N-[ep(oxy-2'-oxo-ethano)-N-methylimino)]-$\Delta^{16}$-5β-pregnene (IR: 3,500 (broad) and 1,635), which are acetylated, without purification, in 4 ml of acetic anhydride-pyridine (1:1) mixture overnight at room temperature. The whole is then evaporated in vacuo and the residue is chromatographed in ethyl acetate-methanol (9:1) solution. This yields 47 mg of crystals of (20S)-3β-methoxy-3α,9α-oxido-7α-hydroxy-11α,20-diacetoxy-14β0, 18 N-[ep-(oxy-(2'-oxoethano)-N-methylimino)]-$\Delta^{16}$-5β-pregnene, which melt at 254°–255°C after one crystallisation. $[\alpha]_D$ = +114° (0.40). IR: 3,510, 2,860, 2,840, 1,730, 1,635 and 1,240.

30 mg of the product thus obtained, in 0.9 ml of absolute pyridine and 0.02 ml of $SOCl_2$, are left for 2 hours at room temperature. The mixture is then poured into aqueous $NaHCO_3$ solution and extracted with ethyl acetate, and the extract is washed with saturated aqueous NaCl solution until neutral. The crude product which arises after drying and evaporation of the organic phase is purified by means of preparative thin layer chromatography, in ethyl acetate as the migrating agent system. This yields 15 mg of (20S)-3β-methoxy-3α, 9α-oxido-11α, 20-diacetoxy-14βO, 18N-ep[(oxy-(2'-oxo-ethano)-N-methylimino)]-$\Delta^{7,16}$-5β-pregnadiene in the amorphous form, which according to thin layer chromatography is a single substance. IR: 2,840, 1,730, 1,650 and 1,635 (double band) and 1,250.

19 mg of this product in 3 ml of absolute ether are boiled for 5 hours with 40 mg of $LiAlH_4$. The excess hydride is then destroyed by carefully adding saturated aqueous $(NH_4)_2SO_4$ solution and the mixture is subsequently poured into 5 per cent strength aqueous $NH_3$ solution. It is then extracted with ethyl acetate and the organic phase is washed with saturated aqueous NaCl solution until neutral, dried and evaporated in vacuo. The resulting crude product is purified by means of preparative thin layer chromatography in the system cyclohexane-chloroform-triethylamine-methanol (16:4:1:1). This yields 10 mg of (20S)-3β-methoxy-3α,9α-oxido-11α,20-dihydroxy-14βO, 18N-[epoxyethano-N-methylimino)]-$\Delta^{7,16}$-5β-pregnadiene, which is a single substance, in the amorphous form. IR: 3,340, 2,840, 1,100 and 990.

10 mg of this product in 1.5 ml of 90 per cent strength aqueous acetone are boiled with 1.5 mg of p-toluenesulphonic acid for 1 hour. The mixture is then added to dilute aqueous 5 per cent strength $NH_3$ solution and extracted with ethyl acetate, and the extract is washed with saturated aqueous NaCl solution until neutral. The crude batrachotoxinin A resulting after drying and evaporation of the organic phase is preparatively purified on thin layer plates in the system cyclohexane-chloroform-triethylamine-methanol (16:4:1:1). This yields 5 mg of batrachotoxinin A in the amorphous form, which proves identical with natural batrachotoxinin A according to a thin layer chromatogram in the systems cyclohexane-chloroform-triethylamine-methanol (16:4:1:1 or 16:4:1:2) and ethyl acetate-methanol (4:1) and according to the IR spectrum, mass spectrum and NMR spectrum.

The NMR spectrum of natural batrachotoxinin A published by Witkop (Journal of the American Chemical Society 91, 3,931 (1969)) is the spectrum of the corresponding deuterochloride which has been produced, prior to the NMR recording, in deuterochloroform contaminated by deuterohydrochloric acid. Apart from this, various signal allocations additionally had to be changed. The NMR values for synthetic and natural batrachotoxinin A are: NMR.: 0.88/s $CH_3$-19, 1.40/d/J = 7 $CH_3$-21, 2.30-2.80/div. bm $CH_2$ = 2', 2.32 + 3.21/2d/$J_{15,15}$ = 19 (additional fine structure due to $J_{15,16}$ = 3 or 2) $CH_2$ = 15 (on irradiation with the frequency of the olefine proton CH-16 the two additionally resolved doublets are simplified to two doublets with $J_{15,15}$ = 19). 2.35/s $NCH_3$, 2.71/s $CH_2$-18, 3.78/d/$J_{11,12\alpha}$ = 9 (additional fine structure due to $J_{11,12\beta}$=4), CH-11, 3.55+4.05/2m $CH_2$-1', 4.46/q/J = 7 CH-20 (on irradiation with the frequency of $CH_3$-21, the signal simplifies to a singlet), 5.66/m CH-16, 6.24/d/$J_{6\beta,7}$=6 (additional fine structure due to $J_{6\alpha,7}$ = 2) CH-7 [$CDCl_3 + D_2O$]. ]

MS (mass spectrum) $M^-$=417 (3.5%), 330 (100%).

EXAMPLE 17

The conversion of the product obtained in Example 9 into 3-0-methyl-7,8-dihydroepi-batrachotoxinin A can be carried out as follows:

200 mg of (20R)-3β-methoxy-3β, 9β-oxido-11β, 20 diacetoxy-14-β-methyl thiomethoxy-18-oxo-Δ16 -5β-pregnene in 4 ml of absolute benzene are warmed with 2 ml of saturated methylamine solution in benzene for 7 hours to 80°C in a bomb tube. The mixture is then cooled and evaporated in vacuo. The resulting 205 mg of the crude Schiff's base of the aldehyde employed, in 15 ml of methanol, are reduced with 200 mg of sodium borohydride in 1 ml of water for 10 minutes at 15°C. The mixture is then worked up and the resulting amine (200 mg) is dissolved in 20 ml of alcohol-free chloroform. 1.5 ml of chloroacetyl chloride and 140 mg of sodium hydroxide in 20 ml of water are added to this solution at 0°C, with vigorous stirring. After 15 minutes the mixture is worked up. This yields 250 mg of crude 3β-methoxy-3α, 9α-oxido-11α, 20-diacetoxy14β-methyl-thiomethoxy-18-(N-methyl-N-chloroacetyl-amino)-$\Delta^{16}$ -5β-pregnene, which is again left, without purification, for 2 hours at room temperature in 20 ml of 0.05 N absolute HCl in methanol. Working up again, and chromatography in benzeneethyl acetate (1:1) solution, finally yields 80 mg of crystalline (20R)-3β-methoxy-3α,9α-oxido-11α, 20-diacetoxy-14β-hydroxy-18-(N-methyl-N-chloroacetyl-amino)-$\Delta^{16}$ -5β-pregnene, which after purification by crystallisation has a melting point of 176°–178°C, optical rotation $[\alpha]_D$ = +35° (0.29) and IR bands 3,350 (broad), 1,725, 1,640 and 1,245, and which is identical with the compound described in Helvetica Chimica Acta 54, page 2,793 (1971) and referred to as 3β-methoxy-3α, 9α-oxido-11α, 20ξ-diacetoxy-14β-hydroxy-18-(N-methyl-N-chloroacetyl-amino)-$\Delta^{16}$-5β-pregnene.

The conversion of this product, according to the instructions in Helv. Chimica Acta, loc. cit., into the compound described there as 3-0-methyl-20ξ-7,8-dihydrobatrachotoxinin yields the 20R-epimer of 3-0-methyl-7,8 dihydroepi-batrachotoxinin A, from which 7,8-dihydro-epibatrachotoxinin A is obtained by saponification of the etherified hydroxyl group in the 3-position in a manner which is in itself known.

EXAMPLE 18

The conversion of the product obtained according to Example 10 into 7,8-dihydrobatrachotoxinin A can be carried out as follows:

(20S)-3β-Methoxy-3α,9α-oxido-11α,20-diacetoxy-14βmethyl-thiomethoxy-18-oxo-$\Delta^{16}$-5β-pregnene is converted according to the instructions reproduced in the preceding example into (20S)-3β-methoxy-3α,9α-oxido-11α,20-diacetoxy-14β-hydroxy-18-(N-methyl-N-chloroacetyl-amino)-$\Delta^{16}$-5β-pregnene), 213 mg of this amorphous compound being obtained by chromatography in benzene-ethyl acetate (1:1) solution. IR: 3,450 (broad), 1,725, 1,645 and 1,250.

320 mg of NaH dispersion are freed of the adhering mineral oil by washing four times with absolute pentane. The product is then covered with 10 ml of absolute benzene and 228 mg of the above chloroacetate in 10 ml of absolute tetrahydrofurane are added under argon. Finally, one drop of a solution of 20 mg of ethanol in 10 ml of absolute benzene is also added and the mixture is boiled under argon, and whilst stirring, for 6 hours. It is then cooled to 0°C and the excess hydride is carefully decomposed with saturated aqueous $(NH_4)_2SO_4$ solution. Customary working up and chromatography in ethyl acetate finally yield 156 mg of crystals of (20S)-3β-methoxy-3α,9α-oxido-11α,20-diacetoxy-14β0, 18N-[ep(oxy-(2′-oxo ethano)-N-methylimino)]-$\Delta^{16}$-5β-pregnene. Melting point after crystallisation 166°–168°C. $[\alpha]_D = +12°$ (1.14). IR: 1,730, 1,634 and 1,250.

40 mg of the resulting compound are now reduced for 5 hours with 100 mg of $LiAlH_4$ in 10 ml of boiling absolute ether. After destroying the excess hydride by careful addition of saturated aqueous $(NH_4)_2SO_4$ solution, the mixture is added to 5 per cent strength aqueous $NH_3$ solution and worked up in the usual manner. Preparative thin layer separation in the system cyclohexane-chloroform-triethylaminemethanol (16:4:1:1) yields 30 mg of crystals of (20S)-3β-methoxy-3α, 9α-oxido-11α,20-dihydroxy-14β0, 18N-[ep(oxyethano-N-methylimino)]-$\Delta^{16}$-5β-pregnene. Melting point, after one crystallisation, 151°–152°C. $[\alpha]_D = +57°$ (0.33). IR: 3,600, 3,450 (broad), 2,810, 1,105, 1,000 and 960.

36 mg of the compound thus obtained are boiled with 28 mg of p-toluenesulphonic acid in a mixture of 7 ml of acetone and 0.7 ml of water for 1 hour. The mixture is then added to 5 per cent strength aqueous $NH_3$ solution and worked up in the usual manner. Preparative thin layer chromatography of the crude product in the system cyclohexanechloroform-triethylamine-methanol (16:4:1:3) yields 31 mg of crystals of (20S)-3β-hydroxy-3α,9α-oxido-11α, 20-dihydroxy-14β0,18N-[ep(oxyethano-N-methylimino)]-$\Delta^{16}$-5β-pregnene (= 7,8-dihydrobatrachotoxinin A) which when recrystallised once melt at 169°–170°C. $[\alpha]_D = +57°$ (0.64), IR: 3,580, 3,400 (broad) 2,810, 1,100, 1,080, 1,065, 1,030, 1,010, 1,000, 960, 925 and 855.

What we claim is:

1. Process for the manufacture of 20-epimeric $\Delta^{16}$-steroid-14β, 18,20-triols of the formula

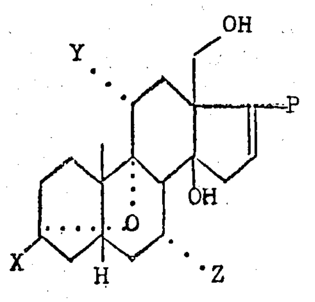

in which formula P represents the 17-pregnane side chain which has one of the two following partial formulae

I

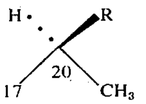

20(S)-configuration

II

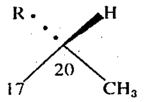

20(R)-configuration wherein R represents a free, esterified or etherified hydroxyl group, X an etherified or esterified hydroxyl group, Y an esterified hydroxyl group, and Z denotes a hydrogen atom or an esterified hydroxyl group, the ester groups being derived from carboxylic acids having up to 18 carbon atoms and the etherified hydroxyl groups being derived from alcohols having up to 8 carbon atoms, characterised in that a corresponding $\Delta^{16}$-20-oxosteroid-14β, 18-diol of the pregnane series in which the 14,18-diol grouping is ketalized with a ketone of the formula

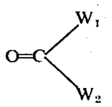

wherein $W_1$ and $W_2$ denote two lower aliphatic hydrocarbon radicals with 1–6 C-atoms or denote, together with the carbon atom to which they are bonded, an alicyclic hydrocarbon radical with 5–12 carbon atoms and 5–7 ring carbon atoms, is treated with a complex light metal hydride which reduces an oxo group to a hydroxyl group but which leaves esterified hydroxyl groups intact, a mixture of the 20(S)- and 20(R)- hydroxy compounds being formed, in which the ketalized 14,18-diol grouping is split subsequently by an acid treatment to give the free 14,18-diol grouping.

2. Process as claimed in claim 1, wherein an alkali metal boron hydride is used as the complex light metal hydride.

3. Process according to claim 2, wherein the reaction is carried out at temperatures between −50° and 0°.

4. Process according to claim 1, characterised in that a complex alkali metal-aluminium hydride of the type

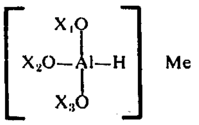

wherein $X_1$, $X_2$ and $X_3$ each denote a tertiary lower alkyl group and Me denotes an alkali metal, is used.

5. Process according to claim 4 wherein the reduction is carried out at temperatures between 0° and 100°.

6. Process according to claim 1, wherein any of the 20-epimeric alcohols obtained is esterified prior to the liberation of the 14,18-diol grouping from the ketalized form.

7. Process according to claim 6, wherein the resulting 20-ester of a 14β,18,20-triol is treated, after having protected any other free hydroxyl groups present, with a sulphoxide of one of the formulae C) 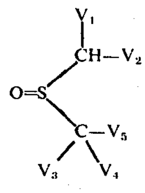 or D) 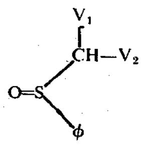

in which formulae $V_1$–$V_5$ denote hydrogen or lower alkyl groups or phenyl-lower alkyl groups and 0 denotes a phenyl nucleus, and a lower aliphatic carboxylic acid anhydride in order to dehydrogenate the 18-hydroxyl group to the aldehydo group and to etherify, simultaneously, the 14β-hydroxyl group with a residue of a 2-thiapropanol or a 2-thiaarylethanol, corresponding to the sulphoxide used, and having one of the formulae A) 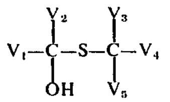 or B) 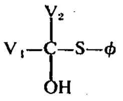

wherein $V_1$–$V_5$ have the meaning given above.

8. Process as claimed in claim 1, wherein a mixture of dimethylsulfoxide and acetic anhydride is used as the reagent.

9. A compound of the formula

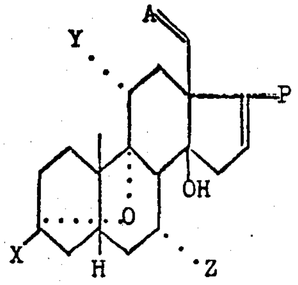

in which P represents a side chain of one of the two following partial formulae

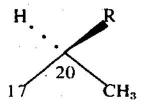

20(S)-configuration

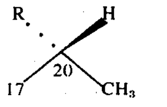

20(R)-configuration wherein R represents a free hydroxyl group or a hydroxyl group esterified with a lower aliphatic carboxylic acid, A represents a hydroxyl group together with a hydrogen atom or an oxo group, X represents a hydroxyl group etherified with a lower aliphatic alcohol with 1–5 C-atoms or esterified with a lower aliphatic carboxylic acid, Y a hydroxyl group esterified with a lower aliphatic carboxylic acid and Z a hydrogen atom or a hydroxyl group esterified with a lower aliphatic carboxylic acid, whereby in compounds, in which A represents the oxo group, the 14β-hydroxyl group is etherified with a 2-thiapropanol of the formula

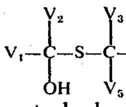

in which $V_1$–$V_5$ denote hydrogen or lower alkyl, and which has up to 8 C-atoms.

10. A compound as claimed in claim 9 which is selected from the group consisting of the 20 R-3β-methoxy-3α,9α-oxido1 1α,20-diacetoxy-14β,18-dihydroxy-$\Delta^{16}$-5β-pregnene, 20 S-3βmethoxy-3α, 9α-oxido-11α,20-diacetoxy-14β,18-dihydroxy-$\Delta^{16}$5β-pregnene, the corresponding 18-oxo compounds, and the 14-ether of same derived from 2-thiapropanol.

11. A compound as claimed in claim 9 and which is a member selected from the group consisting of the 20 S-3β-methoxy-3α,9α-oxido-7α, 11α, 20-triacetoxy-14β,18-dihydroxy-$\Delta^{16}$-5β-pregnene, the corresponding 18-oxo-derivative, and the 14-ether of same derived from 2-thiapropanol.

* * * * *